United States Patent [19]
Greenspan et al.

[11] Patent Number: 6,108,580
[45] Date of Patent: Aug. 22, 2000

[54] APPARATUS AND METHOD FOR STRESS REDUCTION

[76] Inventors: Kenneth Greenspan, 348 E. 51st St., New York, N.Y. 10022; William E. Steiger, Jr., 63 Farm Rd. W., Wading River; Donald J. Hagen, 7 Vista Ct., Phillipsburgh, both of N.J. 11792; Laura G. Terry, 34 Randall Rd., Box #823, Wading River, N.J. 11792

[21] Appl. No.: 09/032,546

[22] Filed: Feb. 26, 1998

[51] Int. Cl.$^7$ .................................................. A61N 1/20
[52] U.S. Cl. ............................. 607/74; 607/75; 607/72; 600/26
[58] Field of Search .................................. 607/68, 70, 72, 607/74, 75; 600/26, 27

[56] References Cited

U.S. PATENT DOCUMENTS

| | | |
|---|---|---|
| 3,762,396 | 10/1973 | Ballentine et al. ............. 600/26 |
| 4,018,218 | 4/1977 | Carlson et al. ................. 600/26 |
| 4,019,510 | 4/1977 | Ellis .................................. 607/75 |
| 4,227,516 | 10/1980 | Meland et al. ................. 600/26 |
| 4,418,687 | 12/1983 | Matsumoto et al. .......... 600/26 |
| 4,664,118 | 5/1987 | Batters ............................ 607/75 |
| 5,342,410 | 8/1994 | Braverman ..................... 600/26 |
| 5,899,922 | 5/1999 | Loos ................................. 607/2 |

*Primary Examiner*—Kennedy Schaetzle
*Attorney, Agent, or Firm*—Kramer Levin Naftalis & Frankel LLP

[57] ABSTRACT

An apparatus and method for applying an electric current to surface layers of a body is described to relieve stress and increase muscle relaxation. The invention provides muscle relaxation and stress reduction by applying an alternating positive and negative d.c. low voltage of substantially equal duration and substantially equal voltage to the skin surface layers. The voltage may be applied at a rate of about 0.2 cycles per second to about 500 cycles per second, with a voltage with a range of about 7.5 volts to about 24 volts, and an amplitude from about 50 microamps to about 1 milliamp.

17 Claims, 6 Drawing Sheets

APPARATUS AND METHOD FOR STRESS REDUCTION

BACKGROUND OF THE INVENTION

1. Field of Invention

The present invention generally relates to an apparatus and method for reducing stress. By using the apparatus and method described herein, a user can apply an electric current to the surface of the skin and thereby induce muscle relaxation.

2. Description of the Related Art

Stress, along with its related muscle spasms and tensions is ubiquitous in today's world. Many devices have been used to relax an individual's muscles and thereby relieve stress. Several devices have been employed which apply varied amounts of low level voltage and amperage to an individual for this and other maladies. There are other devices on the market that generate low-level pulsed electrical currents, but these devices are not used to stimulate the skin, producing dermatones that induce relaxation. These other devices use Cranial electrotherapy stimulation (CES) applied to the head for medical and or psychological purposes. CES signals are transmitted by placing electrodes bitemporally, forehead to posterior neck, or through the earlobes and focus on specific points in the body similar to acupuncture to produce local effects of relieving pain.

Still other devices use probes with relatively high current density output, (Eg. several hundred microamps through a 0.25 inch diameter probe) to specifically relieve pain in local areas; such as, elbows, ankles, knees, etc. Most of these have turned out to be nostrums or only to work by some sort of "placebo effect." There is therefore a great need in the art for an effective muscle relaxation device for relieving stress. The few devices that have shown some causal healing have used local application of low level electricity, wherein the electricity is not applied in the manner contemplated herein. It has been found that applying the particular electrical signal described by the present invention, to the surface of the skin yields general muscle relaxation. More particularly, an improved muscle relaxation device and stress reduction method is provided which applies an alternating positive and negative d.c. low voltage to the skin surface layers.

SUMMARY OF THE INVENTION

According to one aspect of the invention, a device and method for applying electricity to the surface layers of a body is described herein. The device has a means for generating a direct current signal having alternating substantially equal positive and negative voltage. The device also has means for applying said signal to the surface layer of the body.

As will be appreciated by those persons skilled in the art, a major advantage provided by the present invention is applying substantially equal positive and negative voltages of relatively low levels of current to the surface layers of a body. It is therefore an object of the present invention to induce general muscle relaxation by the application relatively low flux rates to the surface layer of the skin of a body. Additional objects of the present invention will become apparent from the following description.

The method and apparatus of the present invention will be better understood by reference to the following detailed discussion of specific embodiments and the attached figures which illustrate and exemplify such embodiments.

DESCRIPTION OF THE DRAWINGS

A specific embodiment of the present invention will be described with reference to the following drawings, wherein.

DESCRIPTION OF THE PREFERRED EMBODIMENT

The following preferred embodiment as exemplified by the drawings is illustrative of the invention and is not intended to limit the invention as encompassed by the claims of this application. An apparatus and method for reducing stress by applying electricity to the body is disclosed herein.

Figure 1:
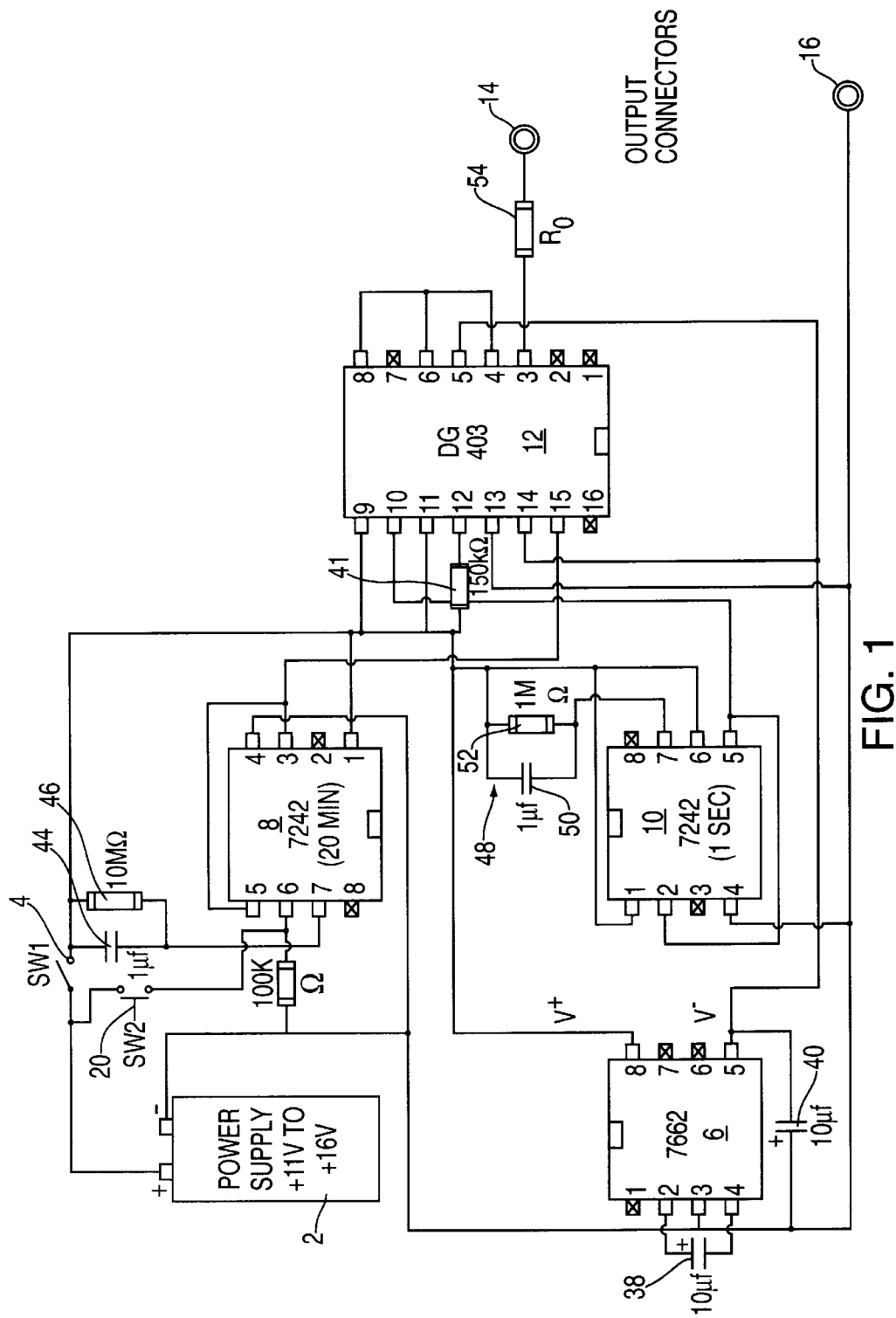
FIG. 1 is a basic wiring diagram of the device of the present invention.

The apparatus 1, as generally shown in FIG. 1, comprises a power supply 2. One terminal of the power supply 2 is connected to a switch 4. The other terminal of the power supply is connected to and supplies voltage to a voltage inverter 6, a long range timer 8 and a short range timer 10. An analog switch 12, is in turn, connected to the voltage inverter 6, the long range timer 8, and the short range timer 10. One output connector 14 is connected to the analog switch 12 and a second output connector 16 is connected to the power supply 2.

Figure 2:
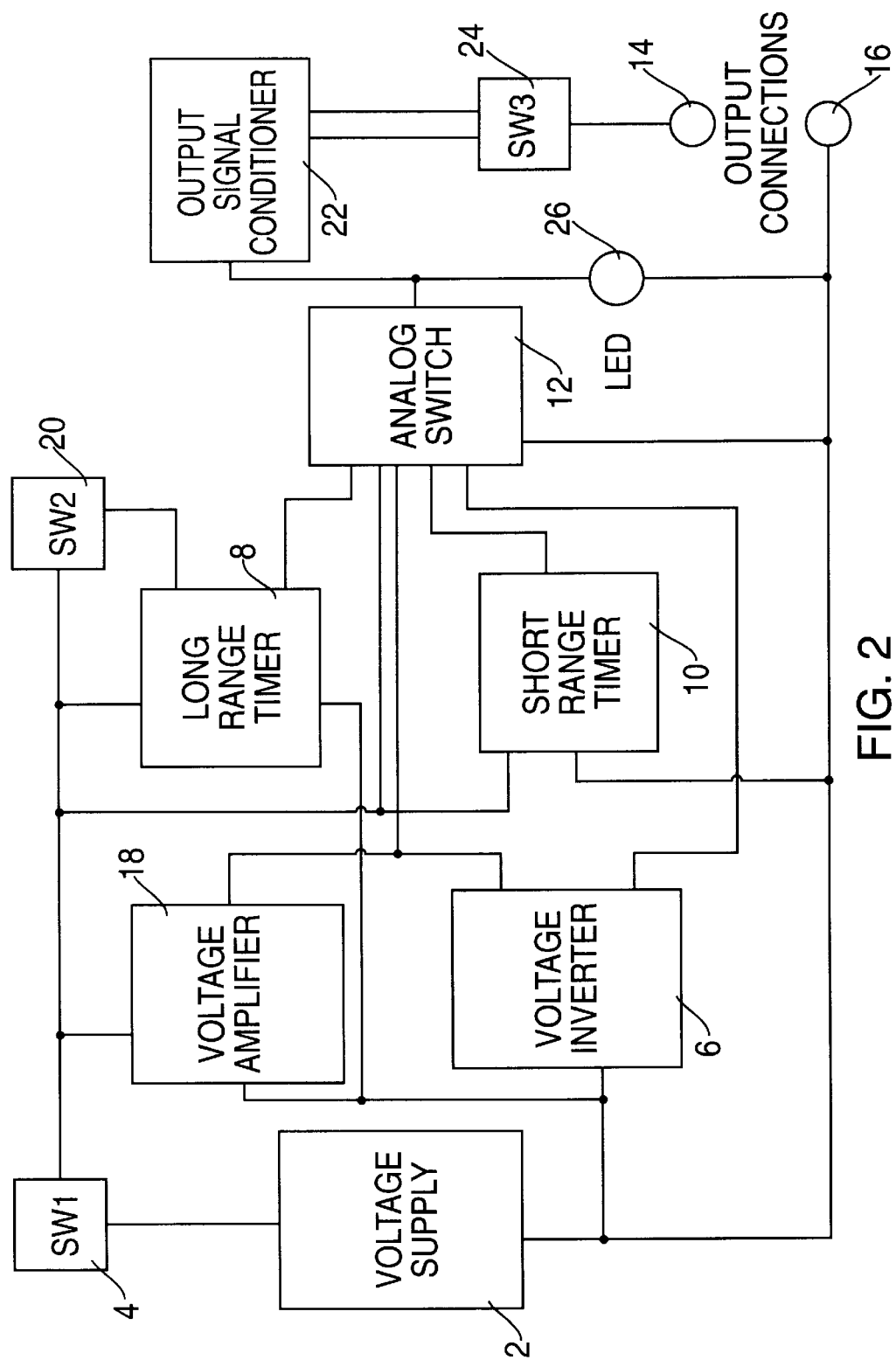
FIG. 2 is a diagrammatic depiction of the functional components of the device of the preferred embodiment of the present invention.
Figure 3:
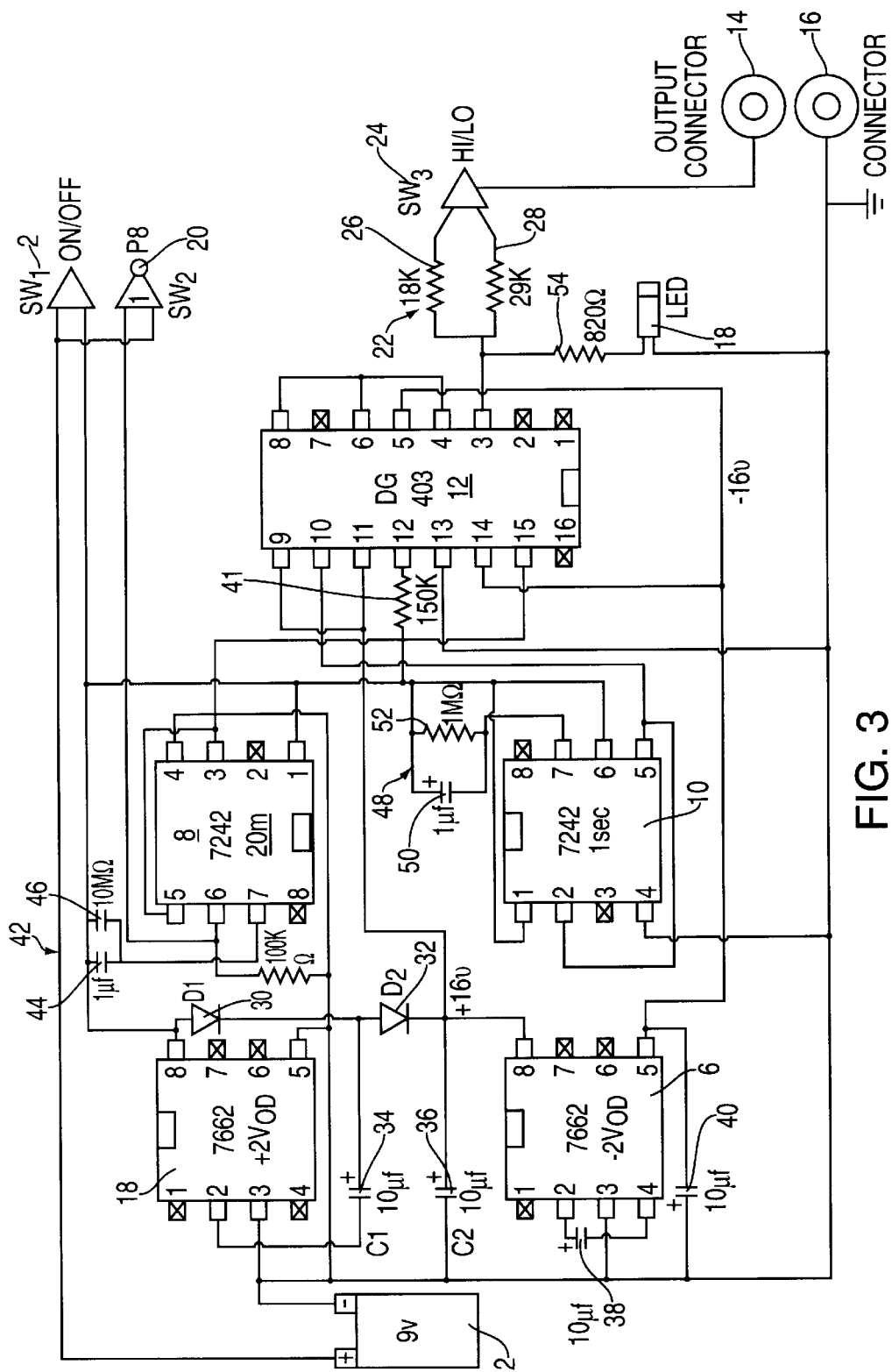
FIG. 3 is a detailed wiring diagram of the device of the preferred embodiment of the present invention.

Referring to FIGS. 2 and 3, a preferred embodiment of the present invention is shown. In this embodiment, a voltage amplifier 18 is interposed between the power supply 2 and the voltage inverter 6 and the analog switch 12. The voltage amplifier 18 increases the power supply voltage to the voltage inverter 6. The voltage inverter inverts the positive d.c. operating voltage to an approximately equal d.c. negative operating voltage. A switch 20 is also included and is connected to the long range timer 8. The short range timer 10 operates a pair of switches within the analog switch 12 for selecting either the positive or the negative operating voltage in an alternating pattern to create a specified positive and negative short cycle signal. The output from the short cycle switches is connected to another pair of switches within the analog switch 12 and are controlled by the long range timer 8. Further included in the embodiment shown in FIGS. 2 and 3, is a output signal conditioner 22. The output signal conditioner 22 is for reducing the output current to the output connection 14 and 16. An output selector switch 24, permits selection of various output current levels. An LED indicating light 26 is connected to the analog switch 12 and the output signal conditioner 22 for indicating that the apparatus is functioning. This is accomplished by connecting the LED indicating light 26 to the positive voltage portion of the operating cycle.

The output signal conditioner 22 is for reducing the output current to the to output connector 14. Reducing the output current can be accomplished in a wide variety of ways, as is well known in the art. As shown in FIG. 3, the output signal conditioner comprises two sets of resistors 26 and 28, of 18 kΩ (kilo ohms) and 39 kΩ, respectively. The switch 24 switches the current between these two resistors resulting in a high or low output current. Alternatively, a current limiter may be used as the output signal conditioner 22. In this way the output signal conditioner can be either a series of resistors or current limiting diodes which are aligned and parallel and are connected on one side to the analog switch 12 and on the other side to the switch 24. The switch 24 provides a select function when more than one current output is sought. Only one resistor or diode at a time can be selected by the output selector switch 24 for passing the operator signal to the output connector 14. The signal conditioner preferably allows the output current to be varied from about 200 μA (micro amps) d.c. to about 750 μA d.c.

Referring to FIG. 3, the power supply 2 is typically provided by a standard d.c. battery having nominally 9 volts. Of course, the power source can be of a wide variety of types, for example, a 12 volt or a 15 volt battery. Alternatively, a lower voltage battery whose output is subsequently amplified to an operating range of from about 11 volts to about 16.5 volts may be used.

As shown in FIG. 3, the preferred embodiment of the present invention has three switches 2, 20, and 24. The switch 2 is typically a simple on/off single pole, single throw (SPST) switch which is used to supply the power source voltage from the power source to the various components of the apparatus. The switch 2 can be of any SPST type device, for example, a toggle switch, slide switch, rotary switch, rocker switch, push-button, or lever handle.

Preferably, the switch 20 as shown in FIG. 3, is a momentary push button switch for providing an external trigger signal to start to the long range timer 8. Although the current trigger input is provided through the external push button switch 20, the external trigger function to the long range timer can also be accomplished by any one-shot means such as a momentary contact device, or a 555 timer chip, or any other chip that can provide a one-shot function.

The switch 24, as shown in FIG. 3, is preferably used when more than one output signal option is desired and is not necessary for the proper functioning of the apparatus as shown in FIG. 2. The switch 24 can be a simple single pole, double throw (SPDT) toggle switch, or can be of any other type of multi-position switch, for example, a rotary select switch with various select positions, a slide switch, or a variable resistor for producing numerous different output signals within the desired operating range.

The long range timer 8 is for determining the operating period of the device of the present invention and can be typically set for a duration in the range of from 0 to about 120 minutes. As shown in FIG. 3, the long range timer 8 is preferably a Harris Corp. ICM 7242 CMOS timer/counter comprising a RC oscillator followed by a 8-bit binary counter.

Referring again to FIG. 3, the voltage amplifier 18 is preferably a Harris Corp. ICL 7662 monolithic high voltage CMOS power supply circuit is used to double the voltage of a 7.5 or a 9.0 volt power supply battery to within the operating range of the device, typically 11 to 16.5 volts. Of course, the same positive operating voltage could be supplied by a battery whose output is within the positive voltage operating range, as is well known in the art. The ICL 7662 voltage amplifier, typically used with any two suitable rectifying externally connected diodes 30 and 32 and two externally supplied 10 μf (micro farad) tantalum electrolytic capacitors 34 and 36. As shown in FIG. 3, this produces an output voltage that is twice the input voltage minus the voltage drop across the diodes.

When used as a positive voltage doubling device, the inverter switches of the ICL 7662 are used to charge the capacitor 34 to a voltage level of V+−Vf (where V+ is a supply voltage and Vf is the forward voltage drop of the diode 30). On the transfer cycle, the voltage on the capacitor 34 plus the supply voltage (V+) is applied through the diode 32 to the capacitor 36. The voltage thus created on the capacitor 36 becomes (2V+−2Vf) or twice the supply voltage minus the combined forward voltage drop of the diode 30 and 32. The output from the voltage amplifier 18 is sent to the voltage inverter 6 and the analog switch 12.

The voltage inverter 6 is preferably an ICL 7662. The ICL 7662 contains all the necessary circuitry to complete the voltage conversion, with the exception of two external capacitors 38 and 40. The two external capacitors 38 and 40 are both preferably 10 μf (micro farads). The ICL 7662 contains two pairs of MOS power switches. These power switches operate with the external capacitors 38 and 34 to perform the inverter function. The input supply voltage to the inverter 6 can come from the voltage amplifier output 18 or directly from a positive battery supply within the apparatus' operating range. The negative output voltage signal of the inverter 6 is sent to the analog switch 12.

In the preferred embodiment of the present invention, both the positive and negative voltage signals are substantially continuous outputs of either the battery or the voltage doubling or inverter chips. Since the efficiency of the voltage converter is typically 99.9%, the positive and negative voltages are preferably substantially equal. Typically, the ICL 7662 chip performs the voltage doubling and inverter functions because its voltage operating range is typically between about 4.5 volts and about 20 volts.

The analog switch 12 receives these substantially continuous positive and negative output signals. By the operation of its internal switches, the analog switch 12 produces an output signal that is of alternating positive or negative voltage. Preferably, the analog switch 12 is a DG 403 monolithic CMOS analog switch as manufactured by Harris Corp. The two sets of internal switches of the analog switch 12 operate independently from signals supplied by different external timing circuits, namely the timing circuit operated by the long range timer 8 and the timing circuit operated by the short range timer 10. The analog switch has about a 44 volt maximum voltage range which permits controlling a 30 volt peak-to-peak signal and which has low resistance variations with analog signals over the +/−15 volt analog input and test range.

The analog switch 12 performs two separate functions. The first function is for generating an output signal from the positive and negative d.c. voltage input signals at the selected frequency (typically in a range from about 0.2 cycles per second to about 500 cycles per second). Preferably, the signal should be applied at a rate in the range from about 0.5 cycles per second to about 2 cycles per second. The second function is to shut off the output signal after the selected operating period, typically about 20 minutes. The operating frequency may be changed from about 0.2 seconds to about 100 seconds and the operating period can be as low as 5 minutes or as long as 120 minutes.

The analog switch 12 is generally operated by the two external timers 8 and 10. Specifically, the first set of switches in the analog switch 12 is operated by the short range timer 10. The short range timer 10 is preferably set to toggle the first set of switches approximately every second thereby passing either a positive or a negative voltage signal to the input of the second set of switches within the analog switch 12. The second set of switches of the analog switch is operated by the long range timer 8. The long range timer is set to toggle the switches typically after about 20 minutes of operation thereby shutting off the output signal from the analog switch to the output connectors 14 and 16 and thereby ending the operating period. The output signal from the analog switch 12 preferably has a maximum range of up to 5000 μA (micro amps) d.c. An external 150 kΩ (kilo ohms) resistor 41 is typically connected to the logic voltage VL input of the analog switch 12 to reduce the positive supply voltage from the power supply to the appropriate reference voltage.

Both timers 8 and 10 which operate the analog switch 12 are preferably Harris Corp. ICM 7242 long range fixed timers. The ICM 7242 is a CMOS timer/counter circuit comprising an RC oscillator followed by an 8-bit binary counter. Its wide supply voltage range of from about two volts to about 18 volts, ease of use and long range timing ability make the ICM 7242 ideally suited for producing a very low frequency square wave.

An external RC timing circuit 42 is typically used in conjunction with the ICM 7242 to produce the desired timing period. For the long range (typically, 20 minutes) a 1.0 μf capacitor 44 and a 10 M Ω (mega ohm) resistor 46 are preferably used. For the short range timer 48 (typically, 1 second) a 1.0 μf capacitor 50 and a 1.0 M Ω resistor 52 are typically used. One side of the 1.0 M Ω resistor 52 is connected to the voltage supply and the other side is connected to the RC input of the ICM 7242 in accordance with the manufacturers recommended connection diagram for astable or "free-run" mode of operation. The manufacturer's timing constant for the ICM 7242 is 128 RC where R is resistance in ohms and C is capacitance in farads. An external trigger is required for the proper operation for the long range timer 8 but is not required for the short range timer 10. In the astable or "free-run" mode, no time "zero" reference point is required. However, in monostable or "one-shot" mode, a time "zero" reference point is required to obtain the proper operating period ($T_p$ on FIG. 4) and is accomplished by utilizing an external trigger to set time "zero".

The signal conditioner connected to the output from the analog switch 12 is for reducing the output current level of preferably between about 4 to about 5 mA (milli amps) to the apparatus' current preferably operating range of from about 50 to about 900 μA (micro amps). The operating range output level is selected to be compatible with various types of devices that can be used to apply the present inventions current and voltage signal to the surface layers of skin. The lower limit of 50 μA (micro amps) is understood as the lower level of effectiveness and the upper level of 900 μA (micro amps) were selected as being the upper limit of comfort.

The light emitting diode 18 is preferably added to the device of the present invention to provide the user with a visual indication that an output signal is being generated and that the long range timer is on. An 820 Ω resistor 54 is preferably placed in series with the LED 18 and is provided to drop the operating voltage of the device to the operating voltage of the LED. Any suitable LED and resistor combination may be selected to perform this indicating function. The polarity of the LED is preferably oriented to operate when the positive voltage portion of the output signal is passing but can be arranged to operate when either the positive or negative portion of the output signal is passing.

The output connectors 14 and 16 can be of several types, for example, snaps, jacks, banana plugs or alligator clips as is well known in the art and depending on the desired end use of the apparatus.

Figure 4:
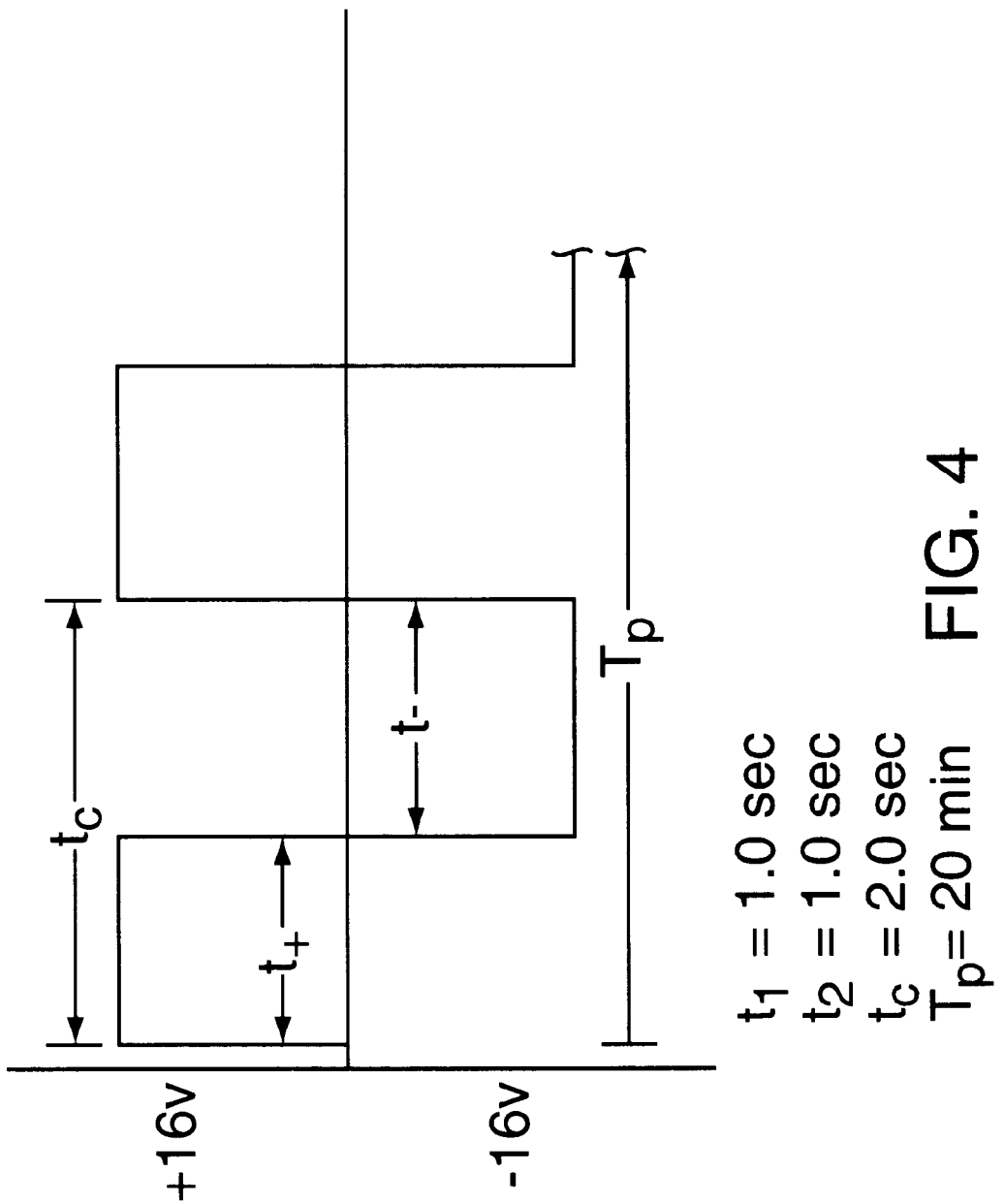
FIG. 4 is a timing diagram showing the graphical output of the device of the present invention.

FIG. 4 represents the output signal from the device. The output voltage (+/−16 volts for the preferred device) is shown on the y-axis and time on the x-axis. The $t_c$ represents the time for a complete output signal cycle where a complete cycle is made up of two components. The t+ is the positive portion and the t− is the negative portion. The duration of t+ and t− are designed to be substantially equal. The positive and negative voltage amplitudes are also designed to be substantially equal. Tp is the total operating period, approximately 20 minutes for the preferred device. The output signal alternates between about 1 second positive voltage and about 1 second negative voltage, and a frequency of about 0.5 cycles per second for the entire operating period. The time for the DG 403 switch to switch from positive to negative and vice versa is 20 nano seconds, essentially instantaneously.

Figure 5:
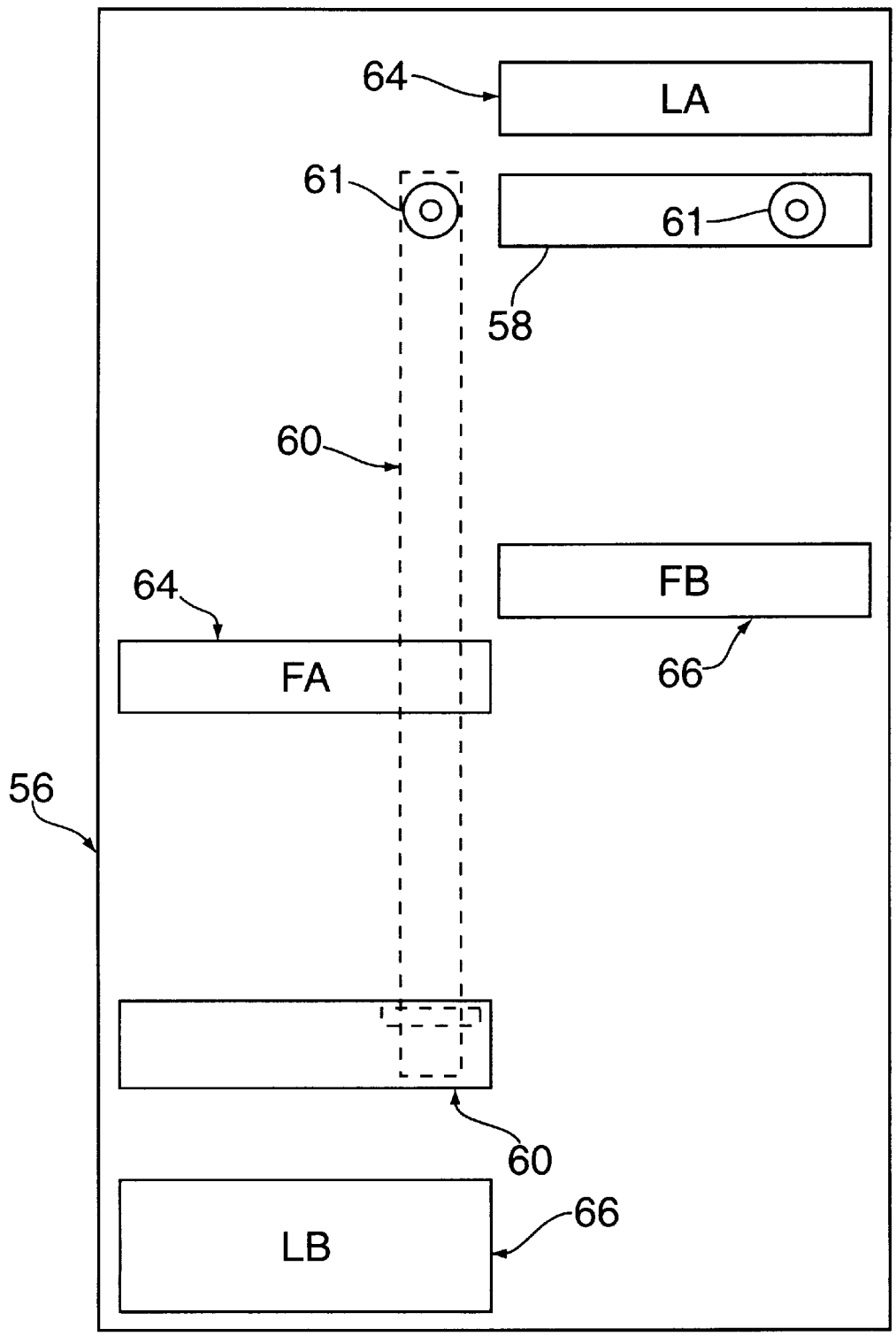
FIG. 5 is a top view of the band of the present invention.

Referring now to FIG. 5, the relaxation band 56 of the present invention is described. The relaxation band is for connection to the output connectors 14 and 16 for supplying the output signal of the device 1 to the surface layers of a body. Conductive strips 58 and 60 on the band 56 are for preferably providing a surface area of approximately 20 square centimeters. When the relaxation band 56 is connected with the operating device it is for preferably reducing the current density in the non-installed position of between about 15 μA per square centimeter and about 35 μA amps per square centimeter. When the band is connected to the device and is installed on the skin surface of a body, the skin surface completes the electrical circuit and current then flows across the surface of the skin between the two conductive strips 58 and 60 of the band 56. The current density levels are preferably in the low micro amp range allowing travel across the surface of the skin thereby stimulating dermatones versus high current density levels.

Dermatones are large sensory areas of skin which communicate via afferent nerves to specific levels of the spinal cord. Sensory nerves travel across the skin, thus allowing us to fill dermatones with our electrical signal. When a dermatome is stimulated by our signal, it communicates to the spine via afferent nerves into a specific spinal "gate". This diminishes other signals such as muscle tension from entering the spinal cord and central nervous system. This diminishes muscle tension and produces a sense of relaxation and wellbeing. As more dermatones are filled and fire off their signals, it is believed that this effect is spread throughout the body and no longer remains a local effect.

The base fabric 62 of the band 56 is preferably a non-conductive material for example, polyester, cotton, or other cloth. The base fabric 62 preferably provides a small amount of stretch to the band 56. The width of the band is typically approximately 3 inches and the length is determined by the size of circumference of the limb to which the band is typically attached. FIG. 5 shows the relaxation band 56 in its open position. Preferably, there are two sets of hook and loop fasteners 64 and 66. The first set of hook and loop fasteners 64 are shown by LA and FA (LA=loop A and FB=fabric A; A=first set of hook and loop fasteners) and securely hold the electrical apparatus to the band 56. Connectors 14 and 16 transfer the electrical signal from the apparatus to the conductive strips 58 and 60 via the band's snaps 61. The band circumvents the apparatus and is held in place by LA and FA fasteners. The second set of hook and loop fasteners 66, shown by LB and FB are for attaching the band to the body. (LB=loop B and FB=fabric B; B=second set of hook and loop fasteners.) Conductive strips 58 and 60 are attached to the band 56 at locations which place them approximately 180 degrees apart when the band is attached to a limb of a person. The powered signal from the device is applied to the conductive strip 60. The current signal then travels across the surface of the skin and is received by the conductive strip 58 thereby completing the circuit. As the current flows from conductive strip 60 to conductive strip 58 along the surface of the skin the afferent nerves sense the signal and transmit it along the surface of the skin. When sufficient skin becomes involved, a dermatome is filled with the signal of the present invention and in turn fires off a relaxing type of signal to the spine similar to the effect felt from a good massage. Gradually more dermatones become filled and fire off their signals to the spine. Because of the continuous low voltage output and alternating positive and negative nature of the signal of the present invention, the relaxing signals fired off by the dermatones overload the spine with positive feeling signals making it very difficult for other competing signals, such as, those related to stress, tension or pain from getting through to the spine (Gate Theory). The spine responds to the relaxing type signals from the dermatones vs those from stress and tension. It is possible for approximately 75% of the non-positive signals to be blocked during this process.

The band is connected to the device by conductive fasteners. Preferably, snap connectors 61 are used to attach the device to the band and for transmitting the device's output signal to the band's conductive strips. The conductive strips 58 and 60 should be chosen to be both a conductive fabric and comfortable. Alternatively, they could be conductive metal strips.

Figure 6:
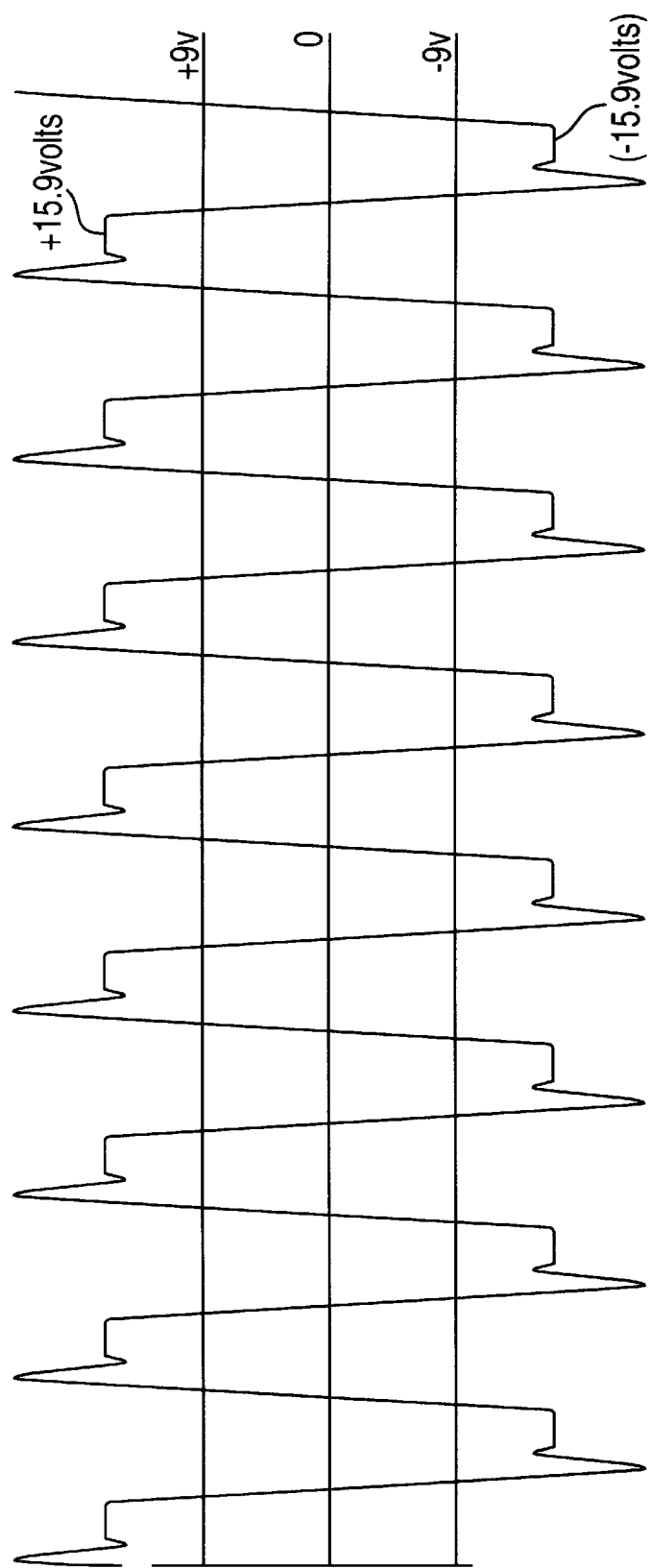
FIG. 6 is a graphical depiction of the output of the present invention.

Referring now to FIG. 6, the analog switch 12 receives the substantially continuous positive or negative output signals and, by the operation of its internal switches, produces an alternating positive and negative output signal for the duration determined by the timing circuit. The net result of the switch operation is to produce a signal which substantially resembles a square wave as shown in FIG. 6. Although the actual signal is not a square wave, it is of a definite and substantially equal positive and negative output repeated as determined by the timing circuit.

FIG. 6 shows an actual trace of the device's output signal as plotted on an x-y recorder. The voltage trace shows substantially equal positive and negative output signals at +/−15.9 volts for the preferred device. The output voltage values are a function of the battery supply voltage, voltage amplifier (ICL 7662), its externally connected diode's characteristics, and the voltage inverter. The trace also shows the equal duration of the positive and negative portions of each cycle. The spike and dip at the beginning of each voltage cycle is due to the high inertia of the recorder pen as it attempts to quickly (20 nano seconds) move from peak to peak voltage.

The objective is to stimulate the skin by passing a flow of current through it. To do this, there must be a potential difference between the conductive strips where a single device is used, or between the devices when two devices are used. The RF signal would synchronize the output signals of the devices so that when one device has a positive output signal, the other has a negative output signal. If the signals were in phase with each other no current would pass between them.

The combination of the high efficiency of the ICL 7662 as a voltage inverter 6 and the short range timer 10 of the ICM 7442 cycle timer operating the switches of the DG 403 analog switch 12 produces a very precise and consistently reproducible output signal. The substantially equal positive and negative voltages combined with the substantially equal operating time of each voltage is a hallmark of the present invention.

Although the particular embodiments shown and described above will prove to be useful in many applications in the muscle relaxation and stress reduction art to which the present invention pertains, further modifications of the present invention will occur to persons skilled in the art. All such modifications are deemed to be within the scope and spirit of present invention as defined by the appended claims.

We claim:
1. A device for applying electricity to a body, comprising:
   (a) means for generating a direct current signal having alternating substantially equal positive and negative voltages of substantially equal duration; and
   (b) means for applying said signal to skin surface layers of the body to stimulate the skin by passing a flow of current through it from a first conductor to a second conductor, wherein said signal is applied in the range of from about 50 $\mu$amps to about 1 milliamp.
2. The device of claim 1, wherein said signal is applied at a rate in the range of from about 0.2 cycles per second to about 500 cycles per second.
3. The device of claim 2, wherein said signal is applied at a rate in the range of from about 0.5 cycles per second to about 2.0 cycles per second.
4. The device of claim 2, wherein said applied signal has a voltage in the range of from about 7.5 volts to about 24 volts.
5. The device of claim 4, wherein said applied signal has a voltage in the range of from about 11 volts to about 16 volts.
6. The device of claim 5, wherein said applied signal is in the range of from about 350 microamps to about 700 microamps.
7. A device for applying electricity to a body, comprising:
   (a) means for generating a direct current signal having alternating substantially equal positive and negative voltages of substantially equal duration; and
   (b) means for applying said signal to skin surface layers of the body to stimulate the skin by passing a flow of current through it from a first conductor to a second conductor, wherein said signal is applied in the range of from about 50 $\mu$amps to about 1 milliamp, at a rate in the range of from about 0.2 cycles per second to about 500 cycles per second, and a voltage in the range of from about 11 volts to about 16 volts.
8. A method for applying electricity to a body, comprising:
   (a) generating a direct current signal having alternating substantially equal positive and negative voltages of substantially equal duration; and
   (b) applying said signal to skin surface layers of the body to stimulate the skin by passing a flow of current through it from a first conductor to a second conductor, wherein said signal is applied in the range of from about 50 $\mu$amps to about 1 milliamp.
9. The method of claim 8, wherein said signal is applied at a rate in the range of from about 0.2 cycles per second to about 500 cycles per second.
10. The method of claim 9, wherein said signal is applied at a rate in the range of from about 0.5 cycles per second to about 2.0 cycles per second.
11. The method of claim 9, wherein said applied signal has a voltage in the range of from about 7.5 volts to about 24 volts.
12. The method of claim 11, wherein said applied signal has a voltage in the range of from about 11 volts to about 16 volts.

13. A method for applying electricity to a body, comprising:
   (a) generating a direct current signal having alternating substantially equal positive and negative voltages of substantially equal duration; and
   (b) applying said signal to skin surface layers of the body to stimulate the skin by passing a flow of current through it from a first conductor to a second conductor, wherein said signal is applied in the range of from about 50 µamps to about 1 milliamp, at a rate in the range of from about 0.2 cycles per second to about 500 cycles per second, and a voltage in the range of from about 11 volts to about 16 volts.

14. The method of claim 12, wherein said applied signal is in the range of from about 350 microamps to about 700 microamps.

15. A method for stimulating skin surface layers to induce relaxation, comprising:
   (a) applying a direct current signal having alternating substantially equal positive and negative voltages of substantially equal duration to skin surface layers of the body; and
   (b) stimulating the skin surface layers to induce relaxation, wherein said signal is applied in the range of from about 50 µamps to about 1 milliamp.

16. A device for applying electricity to a body, comprising:
   (a) means for generating a direct current signal having alternating substantially equal positive and negative voltages of substantially equal duration; and
   (b) means for applying said signal to surface layers of the body, wherein said signal is applied in the range of from about 50 µamps to about 1 milliamp.

17. A method for applying electricity to a body, comprising:
   (a) generating a direct current signal having alternating substantially equal positive and negative voltages of substantially equal duration; and
   (b) applying said signal to surface layers of the body, wherein the signal is applied in the range of from about 50 µamps to about 1 milliamp.

* * * * *